(12) United States Patent
Tortal et al.

(10) Patent No.: US 6,508,814 B2
(45) Date of Patent: *Jan. 21, 2003

(54) METHOD AND APPARATUS FOR RUPTURING TARGETED CELLS

(76) Inventors: Proserfina R. Tortal, 434 W. Harvard, #5, Glendale, CA (US) 91204; Grace Tortal-Quirong, 434 W. Harvard, #5, Glendale, CA (US) 91204; Rolando A. Quirong, 434 W. Harvard, #5, Glendale, CA (US) 91204; Eleazar R. Tortal, 49 Soyuz Street, Moonwalk Village Las Piñas (PH), 3115; Jocelyn F. Tortal, 49 Soyuz Street, Moonwalk Village Las Piñas (PH), 3115

(*) Notice: Subject to any disclaimer, the term of this patent is extended or adjusted under 35 U.S.C. 154(b) by 35 days.

This patent is subject to a terminal disclaimer.

(21) Appl. No.: 09/188,915

(22) Filed: Nov. 9, 1998

(65) Prior Publication Data

US 2002/0029034 A1 Mar. 7, 2002

Related U.S. Application Data

(63) Continuation-in-part of application No. 08/528,921, filed on Sep. 15, 1995, now Pat. No. 5,833,685, which is a continuation-in-part of application No. 08/212,992, filed on Mar. 15, 1994, now abandoned.

(51) Int. Cl.⁷ ............................................... A61B 18/18
(52) U.S. Cl. .......................................... 606/21; 606/20
(58) Field of Search ................................... 606/20–26

(56) References Cited

U.S. PATENT DOCUMENTS 3,736,937 A * 6/1973 Basiulis ........................ 606/20
5,108,390 A * 4/1992 Potocky et al. ............... 606/21
5,275,595 A * 1/1994 Dobak, III .................... 606/23
5,314,423 A * 5/1994 Seney ........................... 606/20
5,423,807 A * 6/1995 Milder .......................... 606/20
5,520,682 A * 5/1996 Baust et al. ................... 606/24

* cited by examiner

Primary Examiner—Michael Peffley
(74) Attorney, Agent, or Firm—Ashen & Lippman

(57) ABSTRACT

A probe contacts targeted tissue, sometimes while positioned adjacent to nontargeted live tissues. In preferred forms, the probe includes a support that only minimally conducts heat from nontargeted tissues. A very conductive targeted-tissue-contacting element, at an end of the support, is immersed in a liquid cryogen (preferably nitrogen) and then removed for contacting with (e. g., insertion into) the targeted tissue. An ultrathin highly thermoconductive polymeric tubing holds both a very conductive, cold material, forming the targeted-tissue-contacting element, and fine insulating material (e. g. highly insulating elastomer) forming part of the support. The targeted-tissue-contacting element is fashioned to fit the targeted tissue in at least one dimension, and the support to fit nontargeted live tissues (if any) adjacent to which the probe is positioned while contacting the targeted tissue. The probe provides for confined heat exchange with the targeted tissue—as by matching dimensions of probe and targeted tissue, or of support and nontargeted tissue, or insulating the support against heat flow into the probe or from nontargeted tissues; and preferably all of these. The best targeted-tissue-contacting element is a solid cryogen, roughly at liquid-nitrogen temperature; ideally it is solid carbon dioxide, particularly super-sublimated carbon dioxide—cooled to a temperature range characterized by extremely tight crystal bonds.

17 Claims, 1 Drawing Sheet

METHOD AND APPARATUS FOR RUPTURING TARGETED CELLS

CROSS REFERENCE TO RELATED APPLICATIONS

This application is a continuation-in-part of U.S. Application No. 08/528,921, filed Sep. 15, 1995 and now issued as U.S. Pat. No. 5,833,685; which was in turn a continuation-in-part of U.S. Application No. 08/212,992, filed Mar. 15, 1994 (now abandoned). The 1994 application is based on Patent Disclosure #344020, "Rupturing Tumor Cells With Non-Cryogenic Probe", submitted to the Commissioner of Patents and Trademarks on Dec. 6, 1993, and wholly incorporated by reference herein.

BACKGROUND OF THE INVENTION

A recent method of cryosurgical treatment (freezing of tumors) for colon carcinoma and prostate tumors involves liquid nitrogen being pumped into a stainless steel probe that is directly inserted within the tumor. It requires heavy storage of liquid nitrogen and pumping machinery to deliver the liquid nitrogen, and a mechanism to suck out from the probe part of the supplied liquid nitrogen that evaporates into gas.

With the cryogenic temperature derived from liquid nitrogen, tumor cells and the immediately surrounding tissues are then frozen. This procedure has to be accompanied by urethral heating, as the surrounding tissues and especially the urethra are greatly at risk of being frozen.

Results of this method show shrinkage of tumors, limiting the spread of cancer, and eventually death of cancer tissues in some successful cases (Onik, G., *Ultrasound Guided Hepatic Cryosurgery in the Treatment of Metastatic Colon Carcinoma*, April 1990).

The probe should constantly be kept free of nitrogen gas buildup (liquid nitrogen that has evaporated into gas in the course of circulation within the probe and heat exchange with the targeted tumor) so as not to block the flow of liquid nitrogen and boil off the rest. The insulation of the probe is very critical.

Liquid nitrogen boils off easily into gas in the course of circulation within the probe and during heat exchange with the targeted tumor. It is critical to apply and maintain a sufficient coldness to the cells in order to freeze them.

SUMMARY OF THE DISCLOSURE

This invention (consisting of methods and a device) increases the damage and death to the cancer cells in cryosurgery treatment without the heavy and costly machinery.

Method

Current cryosurgical procedure circulates liquid nitrogen within a probe directly in contact with the tumor cells, in hopes that cellular fluids will form crystals of ice which damage the cancer cells. In this invention, in its preferred embodiments, tumor cells are first bloated with water prior to freezing so as to produce not only a much greater quantity of crystals (from added water) but also much bigger and coarser crystals that are more destructive.

It makes use of the fact that water when frozen increases in volume enough to "crack" or damage a closed container completely filled with water. Moreover, it has been shown that in this method through introduction of water, freezing time is shortened since targeted cells contain more pure water that is of higher freezing point than cellular fluids.

Device

Unlike other cryosurgical probes, this device in its preferred embodiments does not circulate liquid nitrogen that poses problems of gas blockage, leaks, and heavy and expensive containers and insulation materials. Instead, what we call "super-sublimated" carbon dioxide is used as the cold source. This super-sublimated carbon dioxide is formed by immersing carbon dioxide in liquid nitrogen until thermal equilibrium (equal temperature, at $-196\,°$ C.) between the two is reached.

This is to lock in or store the cold temperature of liquid nitrogen. Crystal bonds of carbon dioxide are tightened tremendously when in thermal equilibrium with the liquid nitrogen.

As a result, unlike liquid nitrogen that loses its cold temperature (boils and evaporates into gas) so easily in the course of circulation within the probe and heat exchange with tumor cells, this super-sublimated carbon dioxide is more efficient. in retaining its cold temperature. Any heat absorbed is not used up to raise its temperature but is used to weaken its crystal bonds.

The cold storage then is the extremely tight molecular bonding of the super-sublimated carbon dioxide. With this mechanism, the use of super-sublimated carbon dioxide as the cold source instead of liquid nitrogen does not require heavy and costly cold storage and insulating material.

In addition heat exchange is confined only within the tumor. This probe does not directly apply its cold temperature in any surroundings other than within the tumor area.

Unlike cryoprobes in which the cold source (liquid nitrogen) passes throughout the probe, a greater portion of which is positioned outside the targeted tumor and outside the body, the cold source of this probe is confined only within the tumor. The rest of the probe preferably is made up of only highly insulating elastomer.

Thus, the cold source does not directly receive any heat from nearby tissues and environment even if the insulating material is not as highly efficient an insulator as would be ideal. With these features, nearby tissues are kept from being frozen and utilization of the cold source is optimized.

DETAILED DESCRIPTION OF THE PREFERRED EMBODIMENTS

A probe according to a preferred embodiment of the invention has a handle A (FIG. 1), consisting of a highly insulating elastomer. Portion B is made up of ultrathin and highly thermoconductive polymer tubing containing partly super-sublimated carbon dioxide at L1 and partly fine insulating materials at L2.

Portion B is inserted into the body C, with the carbon dioxide L1 positioned within the tumor area D, and the insulator L2 outside the tumor E and spanning the area between the skin F and the tumor. L2 contains insulating material instead of the cold source so that nearby tissues will not be frozen.

A tumor is first bloated with water and then frozen until the volume of water inside is increased significantly, enough to damage and rupture the tumor cells. This method utilizes a unique characteristic of water, namely that when water freezes, its volume increases significantly enough to damage a closed container fully filled with water.

With the introduction of water into the cancer cells prior to freezing, much larger, coarser and greater quantities of crystals (from added water) can be produced within the targeted tumor cells. These crystals are far more destructive than those formed by liquid nitrogen freezing the cellular fluids in the tumor (as in prior cryosurgical treatment of prostate and colon carcinoma). Furthermore, with much higher concentration of pure water within the cells, the freezing point is at a higher temperature and thus freezing time is shortened.

Figure 1:
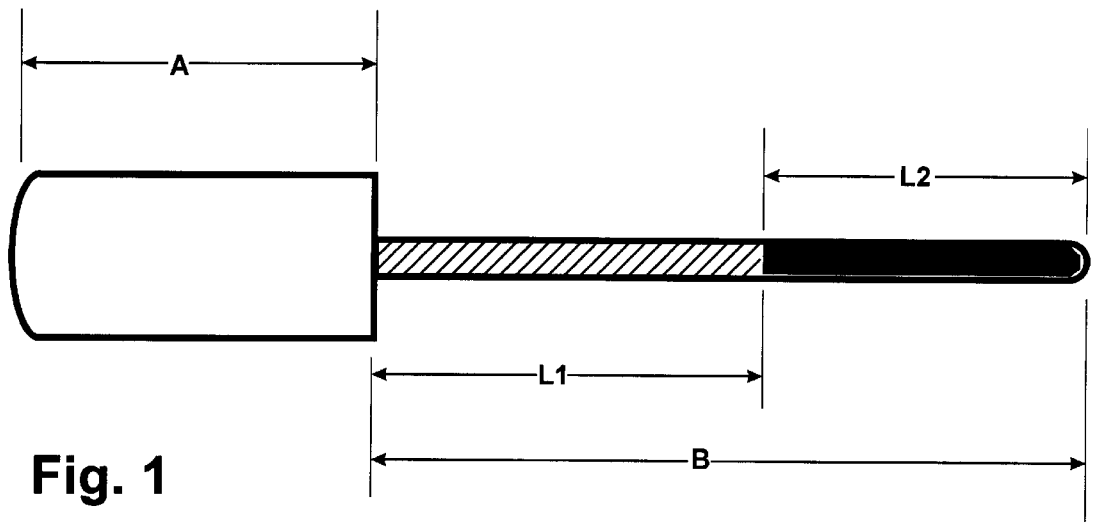
FIG. 1 is a schematic elevational view of a probe according to a preferred embodiment of the present invention.

Freezing is accomplished by the use of a probe (as shown in FIG. 1) containing super-sublimated carbon dioxide (the cold source), carbon dioxide immersed in liquid nitrogen until thermal equilibrium between the two is reached (at $-196°$ C.). It is immersed in liquid nitrogen so as to tremendously tighten the crystal bonds of the solid carbon dioxide.

In this way the coldness is locked in or stored within the carbon dioxide bonding, so that heat coming from tumor cells in contact with the probe is not used to increase the temperature of the solid carbon dioxide (the cold source) but is used to loosen the highly packed crystal bonds of the cold source. Thus, coldness is stored by the super-tight carbon dioxide bonding instead of the heavy and costly cryostat (cryogenic liquid storage) and insulating materials used in prior cryosurgery.

Figure 2:
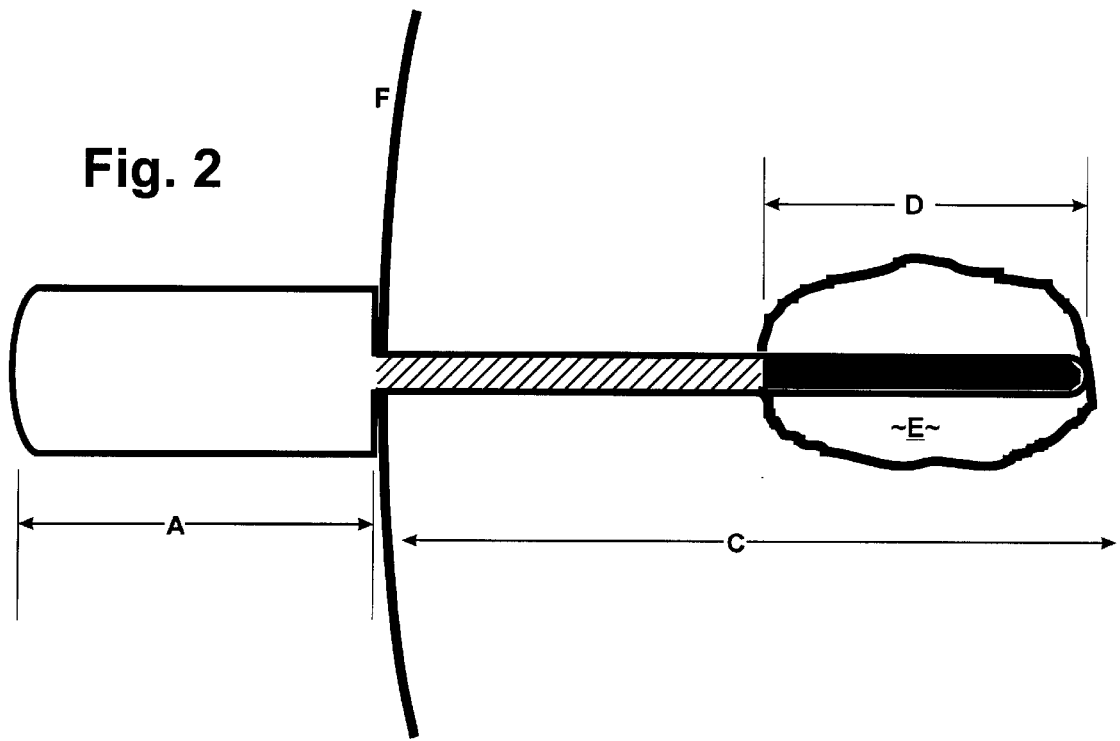
FIG. 2 is a like elevation but partly in cross-section, showing the FIG. 1 probe inserted into a patient's body and into a tumor within the body.

To keep the tissues that are immediately outside the tumor from being frozen and for optimum utilization of the cold source, portion B of the probe that is inserted into the body (see FIG. 2), made of ultrathin, highly thermoconductive polymer tubing, consists of two parts. Part of this tubing, L1 contains the cold source.

This portion is where heat exchange with the targeted tumor takes place, and is positioned within the targeted tumor. The other part of this tubing, L2 contains fine insulating material and is between the skin and the tissues immediately outside the tumor area, so that tissues other than the targeted tumor are not frozen and heat from these tissues does not warm the cold source.

The handle of the probe, portion A, which will be positioned outside the body of the patient, consists of highly insulating elastomer. Accordingly heat from the environment does not enter the cold source.

BEST MODE FOR CARRYING OUT THE INVENTION

For efficient absorption of injected water and its retention within the targeted tumor cells, mannitol is first injected into the targeted tumor. Then water is delivered through a syringe, after which the plunger is pulled out to accommodate a guide wire that is then passed through a needle to the exact location where water has been introduced.

The syringe is then replaced by a dilator, then a cannula. Through the cannula the probe will be inserted. The end of the probe is directed into contact with the exact location where water was injected.

Freezing of water inside the tumor cells begins at this location. The freezing of the tumor is monitored by an ultrasound probe.

To protect the tissues that are immediately outside the tumor from being frozen and for efficient utilization of the cold source, the length of the insulating portion of the polymer tubing is made to vary with the distance of the tumor from the surface skin. Similarly the length of the thermoconductive portion of the tubing of the probe varies with the thickness of the tumor.

By virtue of this relationship the thermoconductive portion of the probe can be confined within only the targeted tumor area for optimum utilization of the cold source. The insulating portion of the tubing should be within the tissues that are immediately outside the targeted tumor so as not to freeze and damage the nearby tissues.

Depending on the volume of the tumor, multiple applications or units of this probe may be necessary to efficiently freeze an entire tumor.

What is claimed is:

1. A therapeutic probe for contacting with targeted tissue that is accompanied on at least one side by nontargeted tissues; said probe comprising:

a support; and a targeted-tissue-contacting element fixed to the support and substantially shaped or dimensioned, or both:
      to have a length that matches a length of the targeted tissue, and
      with respect to said length, to be aligned with the targeted tissue.

2. The therapeutic probe of claim 1, wherein:

the support is for passage through such substantially nontargeted tissues on said at least one side of the targeted tissue.

3. The therapeutic probe of claim 1, wherein:

the targeted-tissue-contacting element is for insertion into position:
      wholly within the targeted tissue, as distinguished from merely lying against the targeted tissue, and
      in direct contact with the targeted tissue, over substantially the entire surface of the targeted-tissue-contacting element.

4. A therapeutic probe for positioning adjacent to nontargeted live tissues while contacting targeted tissue; said probe comprising:

a support that is substantially shaped or dimensioned, or both:
      to have a length that is equal to a depth of such live nontargeted tissues through which the probe must pass to reach such targeted tissue, and
      with respect to said depth, to be aligned with the nontargeted tissue; and a targeted-tissue-contacting element carried on a part of the support.

5. The therapeutic probe of claim 4, for use where the nontargeted live tissues are disposed intermediate between a probe entry point and the targeted tissue; and wherein:

the probe is for insertion through the intermediate nontargeted live tissues before reaching the targeted tissue;

the support is substantially shaped or dimensioned, or both, to fit such intermediate nontargeted live tissues; and the targeted-tissue-contacting element is carried at an end of the support.

6. A therapeutic probe for positioning adjacent to nontargeted live tissues while contacting targeted tissue; said probe comprising:

a support;

a conductive, cold, targeted-tissue-contacting element carried on the support; and means for providing confined heat exchange between the targeted tissue and the probe; and wherein:

the confined-heat-exchange-providing means comprise one or more means selected from the group consisting of:

a probe length that is matched to a length of the targeted tissue, and a support length that is matched to a depth of the nontargeted live tissues through which the probe must pass to reach such targeted tissue.

7. A cryogenic therapeutic probe adapted for positioning adjacent to nontargeted live tissues while contacting targeted tissue, for elimination of such targeted tissue that is malignant or otherwise undesired; said probe comprising:

a support; and a conductive, cold, targeted-tissue-contacting element, adapted for exposure to such targeted tissue and carried on a part of the support, exposure to such targeted tissue; and means for immersion in using a liquid cryogen to cool the targeted-tissue-contacting element preparatory to destructively contacting such targeted tissue;

wherein while in contact with such targeted tissue, the targeted-tissue-contacting element has no direct contact with the liquid cryogen.

8. The therapeutic probe of claim 7, wherein:

the targeted-tissue-contacting element is disposed on an end of the support.

9. The therapeutic probe of claim 7, wherein:

the liquid cryogen is liquid nitrogen.

10. A therapeutic probe adapted for positioning adjacent to nontargeted live tissues while contacting targeted tissue; said probe comprising:

a support; and a solid cryogen, roughly at liquid-nitrogen temperature, carried on a part of the support for use as a targeted-tissue-contacting element; and wherein:

the solid cryogen is solid carbon dioxide, roughly at liquid-nitrogen temperature.

11. The therapeutic probe of claim 10, wherein:

the solid cryogen is super-sublimated carbon dioxide.

12. The therapeutic probe of claim 11, wherein:

the carbon dioxide is cooled to a temperature range characterized by extremely tight crystal bonds.

13. A therapeutic probe for contact with targeted tissue of a patient; said probe comprising:

a substantially nonconductive support for positioning adjacent to nontargeted live tissue of such patient; and at least one very conductive and cold targeted-tissue-contacting element carried by the support; and wherein:

the targeted-tissue-contacting element and support comprise:

an ultrathin, highly thermoconductive tubing, a very conductive and cold material held within a first portion of the tubing, and forming the targeted-tissue-contacting element, and fine insulating material held within a second portion of the tubing, and forming part of the support.

14. The probe of claim 13, wherein:

the tubing is polymeric.

15. The therapeutic probe of claim 14, wherein:

the fine insulating material is a highly insulating elastomer.

16. The therapeutic probe of claim 13, wherein:

the fine insulating material is a highly insulating elastomer.

17. A therapeutic probe adapted for positioning adjacent to nontargeted live tissues while contacting targeted tissue; said probe comprising:

a support; and a solid cryogen, roughly at liquid-nitrogen temperature, carried on a part of the support for use as a targeted-tissue-contacting element; and wherein:

the targeted-tissue-contacting element is carried on an end of the support.

* * * * *